United States Patent [19]
Carson et al.

[11] 4,429,998
[45] Feb. 7, 1984

[54] APPARATUS FOR THE DETECTION OF FAULTS IN CUPS, GLASSES OR THE LIKE
[75] Inventors: David E. Carson, Lawrence; George W. Dalke, Overland Park, both of Kans.
[73] Assignee: Carson/Burger/Weekly, Inc., Lawrence, Kans.
[21] Appl. No.: 303,170
[22] Filed: Sep. 17, 1981
[51] Int. Cl.³ ............................................. G01N 21/88
[52] U.S. Cl. .................................... 356/428; 250/563
[58] Field of Search ............... 356/426, 428; 250/562, 250/563

[56] References Cited
U.S. PATENT DOCUMENTS

| 3,020,033 | 2/1962 | McCreanor et al. | 250/562 |
| 3,533,704 | 10/1970 | Krenmayer | 356/428 |
| 3,859,537 | 1/1975 | Wolf | 250/563 X |
| 4,066,363 | 1/1978 | Juvinall | 356/428 |

Primary Examiner—Robert B. Reeves
Assistant Examiner—Edward M. Wacyra

Attorney, Agent, or Firm—Schmidt, Johnson, Hovey & Williams

[57] ABSTRACT

Improved apparatus is provided for use in detecting faults, such as cracks, "flashes," "short shots" and "grease" deposits, during the quality control inspection phase of the production of molded articles, such as cups, glasses, containers, lids or the like, especially those formed by injection molding from plastic material. The apparatus employs optical sensing and electrical signal handling techniques involving sensors for providing electrical signals (or signal controlling parameters) corresponding to the intensity of light transmitted through or/and reflected from an article being inspected, in conjunction with electrical, fault detection circuitry that responds equally well and produces a fault indicating, electrical output of like polarity for greater than threshold magnitude changes in either direction (decrease or increase) in the intensity of the light being sensed. The apparatus includes sensors permitting the detection of faults in either transparent or opaque articles.

3 Claims, 7 Drawing Figures

APPARATUS FOR THE DETECTION OF FAULTS IN CUPS, GLASSES OR THE LIKE

BACKGROUND OF THE INVENTION

1. Field of Invention

This invention relates to the field of quality control of manufactured items, and, more particularly, to the detection of faults in the production of articles, such as injection molded plastic cups, glasses, containers, lids or the like, by means of apparatus for sensing light (or similar radiations possibly outside the visible spectrum) transmitted through or/and reflected from the article being inspected and for automatically controlling electrical output signals correlated with the intensity of the radiations sensed in such manner that a predetermined amount of change in the level of such signals will indicate the detection of production faults, such as cracks, "flashes," "short shots" and "grease" deposits.

In a more specific sense, however, the invention provides improved apparatus of the mentioned class, which is adopted for reliably responding in a consistent member (i.e., with substantially equivalent electrical output signals) to either increases or decreases in the level of light being sensed from the article being inspected, which in turn further renders it practical to utilize sensor arrangements best suited for detecting various types of faults in diverse types of articles.

2. Description of the Prior Art

It is known that molded articles, such as cups, glasses, containers or the like, and especially those made from plastic materials by injection molding techniques, are subject to various defects or faults during the manufacturing process, particularly cracks in the walls thereof, so-called "flashes" of extra material or typically irregularly shaped areas of undesired excess thickness either adjacent the rim or elsewhere, so-called "short shots" or unintended voids typically in the form of irregularly shaped notches along the rim, and undesired deposits of foreign materials typically in the nature of spots of "grease" or the like upon the walls.

The earliest approach to quality control in the production of such articles involved visual inspection and manual discarding of defective articles by human inspectors; however, that approach proved both relatively unreliable and much too slow to keep up with the rate at which such articles could be fabricated by injection molding techniques. Accordingly, the need was recognized for providing some form of automated and relatively high speed means for detecting the various types of faults that may occur in the production of the mentioned kind of articles and for eliminating those articles determined to be defective from a batch or stream of same to be accepted as meeting desired quality standards.

Known prior proposals or efforts to provide automated testing of the mentioned kind of articles for production defects are illustrated by the Fouse et al. U.S. Pat. No. 3,067,872, the Powers U.S. Pat. No. 3,557,950, and equipment previously made and marketed substantially in accordance with the disclosure of now abandoned U.S. application Ser. No. 48,694 of Carson et al. filed June 14, 1979, to which the reference is made. From the foregoing and our general knowledge of the state of the art, we regard as previously known and do not herein claim as such the broad concept of automated testing for defects of articles such as injection molded plastic cups or the like, the provision of some suitable means implemented by belts, air flow, vibration or other conveying techniques for successively moving articles to be checked to a testing station or zone, the provision of "feeler" or photoelectric means for sensing when an article has been positioned at such station or zone and is ready for testing, the use of mechanical "feeler" means for detecting short shot type defects, the use in general of various arrangements of light sources and photoelectric sensors for sensing variations of the level of light transmitted through or reflected from the article as indicative of various types of defects such as cracks, flashes or grease deposits, the provision of some suitable means for rotationally or otherwise translating the relative positions of the article being tested and the sensors in order to scan various portions of the article in which defects might occur, the provision in general of some suitable means for producing fault indicating electrical control signals in response to light intensity sensings representing a defect, and the provision of some suitable means adapted to respond to such control signals for separating articles detected as having defects from those which were tested to be of acceptable quality.

Prior article testing systems of this general type typically have included a plurality of light intensity sensors, either for the purpose of providing for the detection of different kinds of defects in the article or in order to provide some desired degree of redundancy in the defect detecting functions. Typically, however, known prior systems of such type have been characterized by either a lack of versatility in reliably detecting the various types of faults that may be encountered or relative complexity of the arrangements of sensors and associated electrical circuitry required or both. It has been recognized that such limitations and disadvantages of known prior systems of such type essentially arose from the facts that different types or occurrences of defects will affect the intensity of the light being sensed in differing ways and such effects will also vary or even be reversed by whether transmitted or reflected light is being sensed, together with the tacit assumption in the design of such prior testing systems that either such system or the portions thereof associated with particular sensors would need to be based upon selection of the fault-indicating criterion as being either an increase in light intensity sensed or a decrease in light intensity being sensed, rather than either of those effects in the alternative. This, in turn, effectively became the working assumption in defining such prior systems by virtue of the fact that the electrical circuits being employed in conjunction with the sensors for providing a fault-indicating electrical output in response to a change in the intensity of light being sensed were adapted for effectively responding to a change in the intensity of the sensed light in only a single direction of increase or decrease therein. As a result of such prior approaches and constraining assumptions in connection with the design of prior testing systems of the general type mentioned, those earlier systems have not been well adapted for employment in testing applications in which it may be desirable to use either transmitted light or reflected light or both, nor to reliable testing for all of the types of defects of interest, and it was apparently further assumed by those working in this field, insofar as we are aware, that greater reliability and versatility in such systems would be achievable only through expensive and relatively much more complex arrangements of sensors and associated electrical circuitry of types not really practical for normal quality control applications.

SUMMARY OF THE INVENTION

It is the broad purpose of this invention to overcome the above noted limitations and disadvantages of prior systems for testing articles for production defects through the provision of relatively simple and inexpensive, but highly sensitive and reliable, arrangements of light intensity sensors and associated electrical fault-detecting circuitry adapted for practical quality control applications in which it may be desirable to utilize either transmitted light, reflected light or both for the testing of the particular types of articles to be inspected by the system. It is a further object of the invention to provide an improved article testing system that will respond to a variety of types of different defects that may occur in the production of the articles.

At the heart of the improved testing apparatus provided by the invention is the association with one or more photoelectric sensors of electrical detection circuitry that will respond not only equally well, but also in substantially the same way insofar as the nature of the fault-indicating electrical output from the circuitry is concerned, to either an increase or a decrease in the intensity of the light being sensed. In general, the fault-detecting circuitry thus utilized involves the disposition of the light sensor or sensors in a portion of the circuitry providing an electrical current source, the provision of a current sink in another portion of the circuitry interconnected with the current source at a current summing node, the provision of electrical comparator means coupled with the current summing node and adapted to provide a fault-indicating output when the electrical potential at the current summing node falls below an equilibrium level, and a feedback path from the comparator means portion of the circuitry to the current sink for controlling the latter in a manner such as to normally maintain the potential of the current summing node at its equilibrium level when the sensor or sensors are receiving light of normal intensity indicating an absence of defects, but to produce a change in the potential of the current summing node in one and the same direction relative to the equilibrium level in response to either an increase or a decrease in the intensity of light being sensed by the sensor or sensors.

DESCRIPTION OF THE PREFERRED EMBODIMENT

Figure 1:
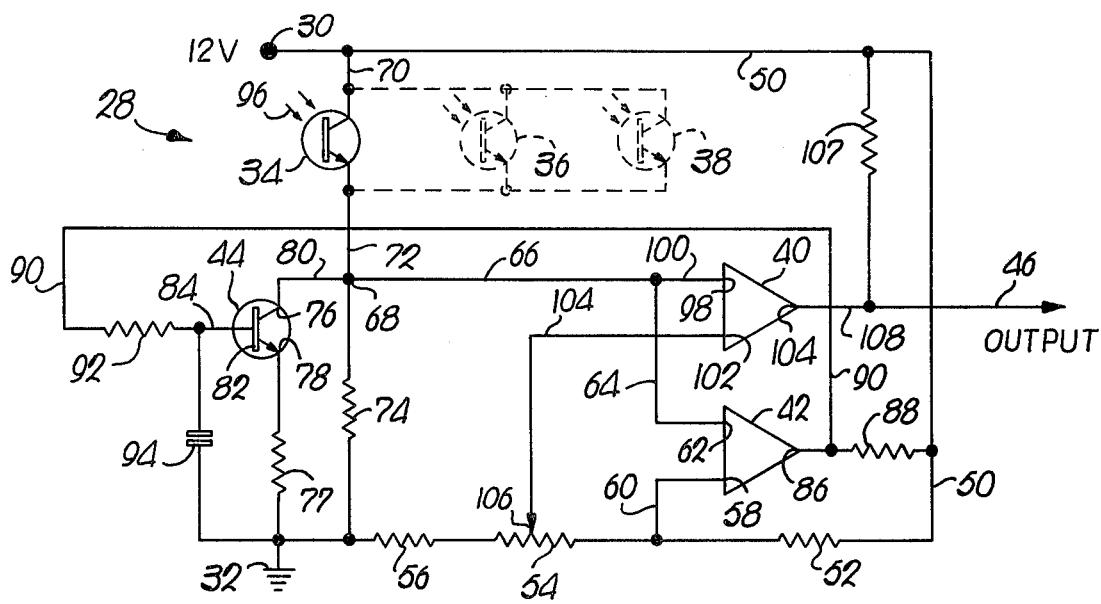
FIG. 1 is an electrical schematic diagram of our currently preferred form of electrical detection circuitry, showing the manner in which it is associated with or incorporates one or more light intensity sensors to which it responds.
Figure 7:
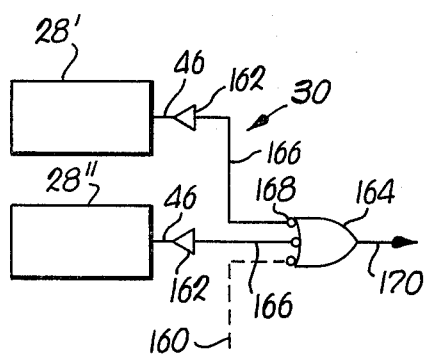
FIG. 7 is a partically block diagram, partially electrical logic device diagram showing the manner in which the fault-indicating outputs from a plurality of electrical fault-detecting circuits of the type shown in FIG. 1 may be combined to provide a master electrical output indicating the detection of a defect in the article being tested by any of the sensors being employed.

The preferred embodiment of the invention to be described for illustrative purposes with reference to the accompanying drawings broadly includes a turntable or the like 12 for supporting and rotating an article 14 to be tested, a light source 16 for use in conjunction with fault sensor assemblies 18, 20 and/or 22 which utilize light from the source 16 that is initially transmitted through at least a portion of the article 14 and then either passes through the remaining portion of the article 14 or is reflected or otherwise diverted therefrom, a combination light source and fault sensor assemblies 24 or/and 26, a number of fault detection circuits as schematically depicted in FIG. 1 and generally designated 28, and a detected fault signal utilization circuit depicted in FIG. 7 and broadly designated 30. As will be apparent, the fault sensors 18, 20 and 22, being dependent upon the transmission of light through at least a portion of the article 14, are particularly adapted for use in testing an article 14 that is transparent or sufficiently translucent to permit the required transmission of light, while the sensors 24 and 26 that are provided with their own associated light sources are adapted for use in testing articles 14 that are either transparent or opaque, since the sensor assemblies 24 and 26 operate from light that is reflected from rather than transmitted through the article 14.

As will be subsequently herein further explained, each of the sensors 18, 20, 22, 24 and 26 is especially adapted for sensing particular types of possible faults and for doing so in a manner which differs from and supplements the fault sensing actions of the other sensors that are being utilized for a particular testing application. At this point in the description, orderliness of explanation would seem to render it appropriate and sufficient to note that the sensors 18 et seq. react to or sense various types of faults in ways that differ in terms of whether an increase or decrease in the intensity of the light being transmitted through, reflected by or diverted from the article 14 is the significant parameter indicating the existence of a fault and, by the same token, whether such fault sensing will be manifested in the form of an increase or a decrease in an electrical current flow or other electrical parameter to be utilized by the detection circuitry portion 28 of the apparatus. Since the nature of the detection circuitry 28 to be employed in the overall combination of elements involved in the apparatus is highly significant to the flexibility of the apparatus in permitting the employment of a plurality of sensors as at 18, 20, 22, 24 and/or 26 for optimumly sensing various types of faults of interest in connection with a particular application of the apparatus, the nature of the preferred detection circuitry 28 will be considered next.

Broadly, the detection circuitry 28 includes a direct current power source represented by a positive voltage terminal 30 and an opposite source terminal as at 32 which may be grounded as illustrated, one or more photosensitive devices as at 34, 36 and 38, a pair of differential voltage comparators 40 and 42, a Darlington amplifier 44 utilized as a current sink, a fault detection signal output line 46, and associated resistance and capacitance elements and electrical interconnections hereinafter more specifically identified. It has been found that the circuitry 28 operates most reliably, if not more than a few devices as at 34, 36 and 38 are associated therewith, so that it should be understood that one of the detection circuits 28 should be employed with each group of, say, four or less related sensor device(s) 34 et seq. associated with each of the sensor assemblies 18 et seq. that is being utilized.

The positive potential of, say, twelve volts available at the terminal 30 is carried by a positive lead 50 to a voltage divider presented by series resistances 52, 54 and 56, the latter of which is connected to ground 32. The values of such resistances 52, 54 and 56 may be chosen so that the continuous reference voltage applied from such voltage divider arrangement to the inverting terminal 58 of the comparator 42 via the lead 60 is maintained at a suitable, predetermined voltage level, such as six volts (in which case the value of the resistance 52 should be equal to the sum of the values of the resistances 54 and 56). The non-inverting terminal 62 of the comparator 42 is coupled via leads 64 and 66 with a current node point 68. The photoelectric sensor device 34 (or a shunted group thereof including additional such devices as at 36 and 38) is coupled between the positive voltage line 50 and the current node point 68 by leads 70 and 72 and presents a light controlled source of electric current flow to the node point 68. The current node point 68 is coupled through a series resistance 74 with ground 32.

The light responsive device(s) 34 et seq. determine the amount of electrical current that will flow through such devices and the leads 70 and 72 to the node point 68 and thence through the resistance 74 to the grounded terminal 32, the preferred choice for the device(s) 34 et seq. being photo-transistor(s), such as the Fairchild Model FPT 130, which respond to an increase in the intensity of light applied to the device by presenting a decreased effective resistance or impedance therethrough premitting a higher level of electrical current to flow therethrough. It will be understood that the positive voltage potential at the node point 68 will be determined by the amount of current flowing through and the resulting voltage drop across the resistance 74.

It will next be observed, however, that the collector and emitter terminals 76 and 78 of the Darlington amplifier 44 are coupled in series between the node point 68 and ground 32 via a lead 80 from the point 68 to the collector terminal 76 and a resistance 77 coupled between the emitter terminal 78 and ground 32. Such last mentioned circuit branch is, of course, in parallel or shunt with the resistance 74, so that the amount of current flowing through the latter, and thereby the voltage potential existing at the node point 68, will be affected (and decreased) by any flow of the total current made available at the node point 68 by virtue of the current passing action of the photosensitive device(s) 34 et seq. which may be permitted to flow to ground through the shunt circuit via the collector 76 and emitter 78 of the Darlington amplifier 44. It will be further perceived, therefor, that the last mentioned path presents a current sink from which at least a portion of the current otherwise made available at the node point 68 may be shunted to ground 32 to whatever extent is permitted by control signals applied to the base 82 of the Darlington amplifier 44. Those skilled in the art will appreciate that the Darlington amplifier 44 has been depicted in the drawing for the sake of simplicity of explanation as if only a single transistor component were involved, but the preferred construction actually employs a National Model MPSA 14 Darlington amplifier assembly. With reference to the depiction in the drawing, however, it will be understood that the internal circuit path between the collector 76 and the emitter 78 is normally non-conducting, so that little or no electrical current will flow therebetween, but that application of a positive potential to the control input (or base 82) of the Darlington amplifier 44 via the lead 84 will cause the amplifier 44 to permit conduction and flow of electrical current between the collector 76 and the emitter 78 thereof in amount dependent upon the level of the positive control input being applied via the input lead 84.

The output terminal 86 of the comparator 42 is coupled through a pullup resistance 88 with the positive voltage line 50 and is also coupled via a lead 90 and an input resistance 92 with the control input lead 84 of the Darlington amplifier 44. Thus, whenever the current flowing to the node point 68 via the device(s) 34 et seq. and the lead 70 and 72, in relation to any current flow away from the node point 68 to ground 32 via the collector-emitter path 76–78 and the resistance 78, is such that the positive potential of the voltage at the point 68, and thereby at the non-inverting input 62 of the comparator 42, would exceed the reference potential applied to the inverting input 58 of the comparator 42 via the reference potential lead 60, a positive voltage output signal will be produced at the output terminal 86 of the comparator 42 and thence applied via the lead 90 and the input resistance 92 to the input lead 84 of the Darlington amplifier 44 that is employed as a current sink control for the node point 68. The application of such a positive control signal to the input lead 84 results in the path between the collector 76 and the emitter 78 becoming conductive to permit the flow of sink current away from the node point 68 through the amplifier 44 and the resistance 77 to ground 32 in an amount sufficient to restore the voltage potential at the node point 68 to the substantially same level as the reference potential being applied via the lead 60 to the inverting input 58 of the comparator 42. Thus, assuming that the reference potential at the terminal 58 of the comparator 42 is six volts positive, the feedback path including the lead 90, the resistance 92 and the current sink amplifier 44 will effectively operate to promptly restore the voltage level at the node point 68 to the quiescent reference level of, say, six volts positive following any temporary excursion of the potential momentarily presented at the node point 68 as a result of a sharp increase in current flow through the photosensitive device(s) 34 et seq. A capacitor 94 is preferably coupled between the input lead 84 of the amplifier 44 and ground 32 to provide with the resistance 92 a resistance-capacitance timing circuit at the input of the amplifier 44, the time constant of which should be selected by the values for the resistance 92 and the capacitor 94 to provide prompt reaction of the amplifier 44 to sharp changes in the level of the control signal applied to its input terminal 82, while diminishing or "smoothing out" the current sinking action of the amplifier 44 to slower changes in the level of the control input signal applied via the input lead 84, which optimizes the circuit 28 for the rapid detection of real faults in an article 14 while remaining appropriately insensitive to relatively slowly changing ambient conditions or the like.

Bearing in mind the mentioned effects of both the intensity of light as at 96 being applied to each of the photoelectric device(s) 34 et seq. and the offsetting action of the current sink amplifier 44 and its associated comparator 42 and feedback path 90 upon the potential level of the voltage at the node point 68, it will be observed that the latter is also coupled with the non-inverting input terminal 98 of the comparator 40 via the lead 66 and a lead 100. The inverting terminal 102 of the comparator 40 receives a reference potential via the lead 104 from an adjustable tap 106 associated with the resistance 54, the latter component being provided by a potentiometer. Presuming that the tap 106 of the potentiometer 54 is adjusted away from the end of the resistance of the latter nearest the positive voltage line 50, as will normally be the case, it will be apparent that the reference voltage level applied from the tap 106 to the reference input terminal 102 of the comparator 40 will be of somewhat lesser level than the reference potential being applied to the reference input terminal 58 of the comparator 42. Thus, adjustment of the tap 106 may be utilized to control the sensitivity of the apparatus by permitting slight variations in the potential applied to the input terminal 98 of the comparator 40 before the operational characteristics of the latter will traverse the "knee" of its voltage transfer characteristics to cause a major change in the level of the potential of the output voltage produced by the comparator 40 at its output terminal 104. The output terminal 104 of the comparator 40 is coupled with the positive supply line 50 through a pullup resistance 107 and is also coupled via lead 108 with the fault detection output line 46 of the circuitry 28.

Figure 2:
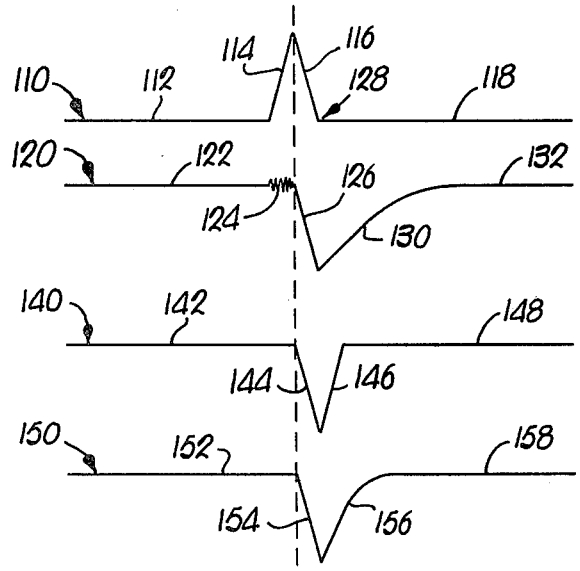
FIG. 2 depicts in somewhat idealized form for simplicity of illustration and explanation pairs of waveforms showing the relationship between the input current applied to the summing node of the circuitry and the potential produced at such node in response to such current, for both the case in which such input current is increased and the case in which such input current is decreased by the action of the associated light intensity sensor or sensors in response to an increase or a decrease in the intensity of light being sensed by the latter.

The operation of the comparator 40, in its relationships to the other parts of the circuitry 28, and under various operating conditions that may occur, can most conveniently be explained with reference to the waveforms or depictions of the varying levels to certain electrical parameters with time illustrated in FIG. 2, which waveforms those skilled in the art will understand are somewhat simplified or idealized to facilitate explanation and ready comprehension of the significant relationships involved. The line 110 in FIG. 2 represents the changing level with time of the flow of current from the current source part of the circuitry 28 including the photosensitive device(s) 34 et seq. and the leads 70 and 72 to the current node point 68, in which the stretch 112 indicates the source current flow to the point 68 during normal quiescent operation of the apparatus with the intensities of the light 96 being applied to the photoelectric device(s) 34 et seq. producing a source current flow corresponding to a lack of sensing of any faults by any of the device(s) 34 et seq., the stretch 114 represents the rising edge of the pulse of increased flow of such source current produced by a fault generated increase in the intensity of light 96 applied to one or more of the sensing device(s) 34 et seq., the stretch 116 represents the falling trailing edge of such source current pulse which occurs as the fault bearing area of the article 14 passes by the line of sensing associated with the previously activated device(s) 34 et seq. and returns to its normal quiescent level as represented by the stretch 118. The line 120 depicts the time correspondent action of the voltage potential at the summing node point 68. While the source current flow to the node point 68 remains at its quiescent, no-fault level as represented by the stretch 112 of the waveform 110, the level of the potential at point 68 similarly remains at a quiescent level represented by the stretch 122 of the waveform 120, which maintains the output from the comparator 40 at a quiescent normal level based upon the operation of the latter adjacently above the "knee" of its operating characteristics. Adjustment of the tap 106 of the potentiometer 54 is utilized to suitably set the voltage differential between the input terminals 98 and 102 of the comparator 40 for operation of the latter in the mentioned relationship of its operating charcteristics for conditions in which the potential level at the node point 68 is at its quiescent value of six volts positive.

Assume next that one or more of the photoelectric sensing device(s) 34 et seq. encounters a fault in the article 14 involving a sharp increase in the intensity of light applied thereto, which in turn results in a sharp increase in the source current flow to the node point 68 represented by the stretch 114 of the waveform 110; in that situation, the increased current flow through the resistance 74 to ground 32 and the corresponding increase in the voltage drop across the resistance 74 will result in a tendency of the potential level at the node point 68 to rise above its quiescent value of, say, six volts. However, any such increased potential at the node point 68 is immediately communicated via the leads 66 and 64 to the input terminal 62 of the comparator 42, which then produces a corresponding output that is fed back via the lead 90 to the current sink amplifier 44, thereby causing the latter to appropriately increase the conduction permitted between its collector and the emitter terminals 76 and 78 to consume or sink that portion of the increased current appearing at the node point 68 required to restore the potential level at the point 68 to its quiescent level of six volts. During such action of the feedback signal from the comparator 42 and the resultant alteration of the current sinking characteristics of the amplifier 44, very small excursions of the voltage at the collector 76 of the amplifier 44 may occur (as indicated with reference to the potential at node point 68 by the slight "zigzagging" of stretch 124 of the waveform 120); however, such excursions are very minor and of the nature typical with the equilibrium seeking characteristics of an electrical feedback arrangement and do not produce either positive going or negative going pulses of sufficient magnitude to cause any significant or recognizable change in the output presented upon the line 46 of the circuitry 28. As soon as the fault area of the article 14 which generated the initial sharp increase in the source current represented by the stretch 114 has passed the involved sensing device(s) 34 et seq., however, the intensity of the light 96 will quickly return to its normal quiescent or no-fault level, thereby concurrently causing the source current flow to the node point 68 to also sharply fall, as represented by the stretch 116 of the waveform 110, to its normal quiescent level represented by the stretch 118. During the sharp falling of the source current level as at 116, the potential level of the voltage at the node point 68 also falls sharply which terminates the production by the comparator 42 of any output to be fed back to the amplifier 44 to support current sinking action of the latter; but the amplifier 44 is capable only of current sinking rather than current sourcing action relative to the node point 68 and, therefore, does not resist a falling voltage level at the point 68. Accordingly, the potential level of the voltage at the node point 68 is permitted to fall below its quiescent level in correspondence with the falling source current level 116, which causes the differential between the potential being applied to the input terminal 98 of the comparator 40 and the reference potential being applied to the reference terminal 102 thereof to "cross back over the knee" of the voltage transfer characteristics of the comparator 40, which further results in a sharp dropping in the voltage level of the output signal fed to the line 46 from the comparator 40. As the source current returns as at 128 to its quiescent level 118, the potential level at the node point 68 will rise back toward its quiescent level of six volts and the output signal from the comparator 40 will also return to the quiescent level of the latter. Thus, it will be clear that the circuitry 28 produced, in response to the sensing of a fault wherein increased light intensity caused increased current flow to the node point 68, a negative pulse 126-130 in the potential at node point 68, which in turn produced negative pulse output at the output line 46 that is well adapted for utilization as an electrical representation of a detected fault.

But, as has previously been indicated or implied, some types of faults to be detected by the sensors 18 et seq. in particular types of articles 14 involve a sharp decrease in the intensity of the light applied to the photoelectric device(s) 34 et seq., rather than an increase therein for which the operation of the circuitry 28 has just previously been described. As also previously pointed out, however, in order to permit the versatility and realiability achieved by the apparatus of this invention, it is necessary that the circuitry 28 employed with the sensors 18 et seq. be able to detect faults manifested by decreases in light intensity 96 with facility equal to its handling of faults represented by increases of light intensity 96 and to do so in a manner that will result in an at least closely similar type of change in the output signals presented to the output line 46, that is, a pulse of the same polarity with respect to the normal quiescent level of the output from the comparator 40 as result from the sensing of faults characterized by an increase in light intensity. The waveform 140 again depicts the level of the source current being supplied to the node point 68, with the stretch 142 representing the normal or quiescent level thereof, but with the stretch 144 representing a sharp decrease in the source current corresponding to a similarly sharp decrease in the intensity of light 96 being applied to the photoelectric device(s) 34 et seq., the stretch 146 representing the return of the source current, after the passage of a fault by the involved sensing device(s) 34 et seq., to the normal or quiescent level of the source current represented by the stretch 148. The waveform of the corresponding potential at the node point 68 is depicted at 150 and includes a stretch 152 representing the quiescent state before a fault is sensed, a stretch 154 representing the sharp decrease in the potential level in response to the concurrent decrease in source current level as at 144, and a stretch 156 representing the return of the potential at point 68 to its quiescent level as represented by the stretch 158, after the fault has passed the involved sensing device(s) 34 et seq. and the intensity of light 96 being applied to the latter has returned to its normal no-fault level. As shown in FIG. 2, the "recovery time" for the potential pulses 126-130 and 154-156 may vary somewhat depending upon the nature of the fault and the particular sensor 34 by which it is sensed. For practical purposes, however, the output producing pulses 126-130 and 154-156 are identical in all relevant respects associated with the indication of detection of any fault by the production of a negative going pulse at the output line 46 from the comparator 40.

Although those skilled in the art may select equivalent or otherwise suitable components for constructing each of the detector circuits 28 that may be required for handling the combination of sensors 18 et seq. to be utilized in a particular application and may also choose to design the circuit 28 with specifically different values for particular resistance and capacitance components, the set of components and component values employed in the preferred embodiment, other than those already mentioned, are as follows. National Semiconductor Model LM 393 differential voltage comparator components are suitable for implementing the comparators 40 and 42. The pullup resistances 88 and 107 may each be 4,700 ohms. The resistance 52 may be 8,000 ohms with the potentiometer 54 having a resistance of 5,000 ohms and the resistance 56 being 3,000 ohms. The resistance 74 is suitably 100,000 ohms, and the resistance 77 may be 47 ohms for the type of Darlington amplifier component 44 previously mentioned. The values for the resistance 92 and capacitor 94 will depend upon the associated time constant that is desired, but respective values therefor of 47,000 ohms and 4.7 microfarads have been found satisfactory in the preferred embodiment. Although it is currently preferred to use photoelectric sensing device(s) 34 et seq. of the previously mentioned or an equivalent type in which an increase in the intensity of light applied thereto results in lowered internal impedance and resulting increased current flow therethrough, it will be clear to those skilled in the art that, with appropriate minor modifications of the associated portions of the circuitry 28, the photosensitive devices 34 et seq. could be implemented with components of the type that internally generate current flow in response to the intensity of light applied thereto or of a type in which an increase in intensity of applied light results in an increase in effective electrical impedance therethrough, if desired, it being observed that such flexibility in the choice of components for implementing the fault sensing device(s) 34 et seq. is one of the virtues of the apparatus resulting from the adaptability of the circuitry 28 to respond with equal facility and by the production of fault detection indicating output signals that are identical in the relevant respects regardless of whether the existence of a fault is sensed in terms of an increase or a decrease in the intensity of light applied to the sensing device or in the alteration of source current flow resulting therefrom. All components of the circuitry are individually conventional and are economically available on the market.

In connection with the electrical aspects of the apparatus involved in the handling and utilization of fault detection indicating signals from a plurality of the circuits 28, as would normally be involved in a typical application utilizing a plurality of the sensors 18 et seq. hereinafter further described, it will usually be desired to "funnel" fault detection indicating signals from all of the involved detection circuits 28 into a common output or signal channel in which a fault sensed by any of the sensing devices 34 et seq. of any of the sensor assemblies 18 et seq. will provide a signal indicating the detection of some fault, which may be used for rejecting the defective article 14 or initiating other appropriate action. Reference is next made, therefore, to FIG. 7 in which a pair of the detection circuits are illustrated and respectively designated 28' and 28", and the dotted line 160 is intended to indicate adaptability for additional circuit 28 being cooperatively associated in a manner similar to that illustrated in solid lines for the circuits 28' and 28". The output line 46 of each of the fault detection circuits 28' and 28" may be coupled through conventional amplifier or other signal modifying circuits 162 for appropriately further shaping the output pulses as at 126-130 or 154-156 presented upon the output line 46 of each detector circuit and for feeding the thus amplified and/or modified fault detection signals to a OR type logic gate or its equivalent 164 via a lead 166 for each of the involved detection circuits 28', 28" etc. Presuming that the signal presented to each of the leads 166 may still be in the form of a negative going pulse for indicating a detected fault condition, a polarity inverter as at 168 may be interposed between each of the leads 166 and the corresponding input of the OR gate 164, and it will be understood that the output presented by the OR gate 164 to its output line 170 would then be in the form of a positive going pulse or relatively positive signal for indicating the detection of any fault, as compared with the output to line 170 from the OR gate 164 being at a lower or neutral value in the absence of any fault being detected.

Figure 3:
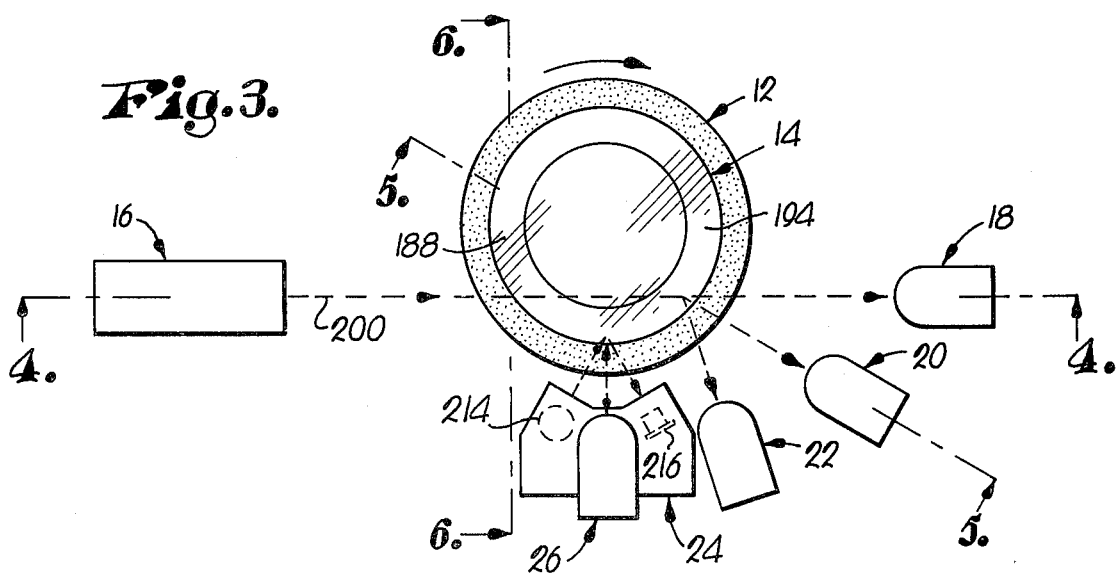
FIG. 3 is a largely schematic, top plan depiction showing the relationship between an article to be tested and various light sources and sensors contemplated by a currently preferred embobiment of the invention adapted for employing either transmitted light sensing or reflected light sensing or both when such redundancy is desired and appropriate for greatest versatility or/and reliability of the testing results, although the employment of less than all of such sources and sensors may be adequate for some particular applications.

Attention is next redirected to FIG. 3 in which the preferred juxtaposition for the turntable 12, the light source 16 and the various sensor assemblies 18 et seq. that may be present for a particular application is shown in a plan view thereof. Those familiar with the art of testing articles 14 such as plastic cups or the like will recognize that the turntable 12 illustrated may be just one of a plurality of same that are carried by a common base (not shown) which can be rotatably indexed to bring each of such turntables 12 and an article 14 to be tested that is carried thereby into the required juxtaposition with the light source 16 and the sensor assemblies 18 et seq. illustrated in the drawing. It will be appreciated, therefore, that the location of the light source 16 and the assemblies 18 et seq. needs to be accommodated to the typical need to successively index a plurality of turntables 12 into the illustrated testing position for the articles 14, as well as to be suited to operably perform the desired testing functions.

Figure 4:
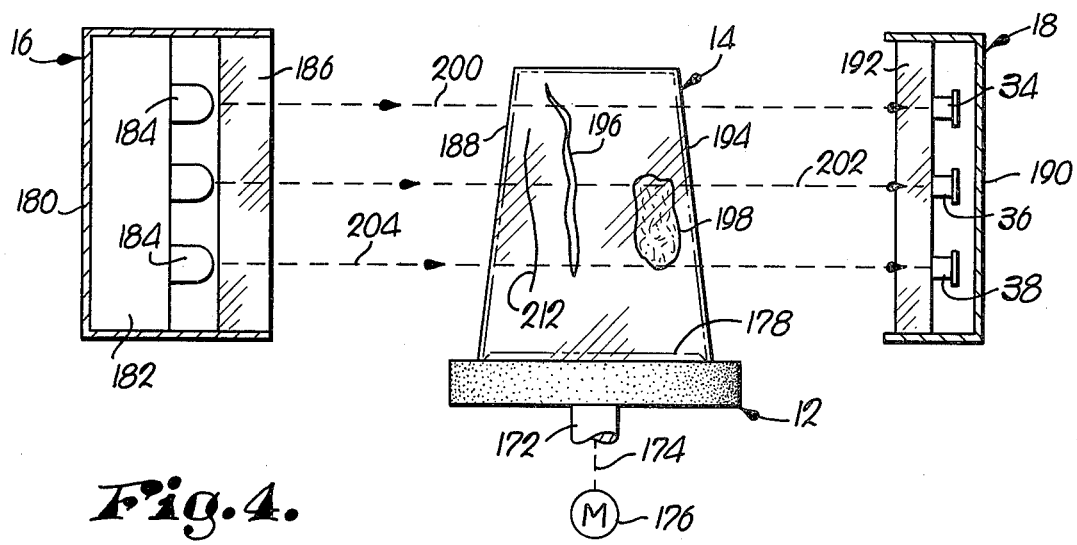
FIG. 4 is a largely schematic, side elevational depiction of a portion of the apparatus shown in FIG. 3, with the sources and sensors being viewed in cross-section along line 4—4 of FIG. 3.
Figure 5:
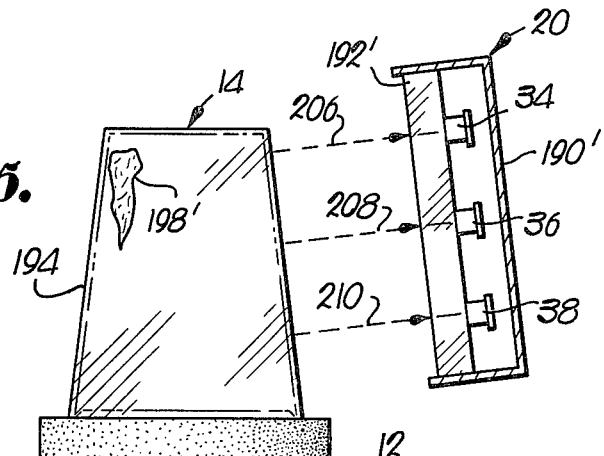
FIG. 5 is a largely schematic, side elevational depiction of another portion of the apparatus shown in FIG. 3, with the sources and sensors being viewed in cross-section along line 5—5 of FIG. 3.
Figure 6:
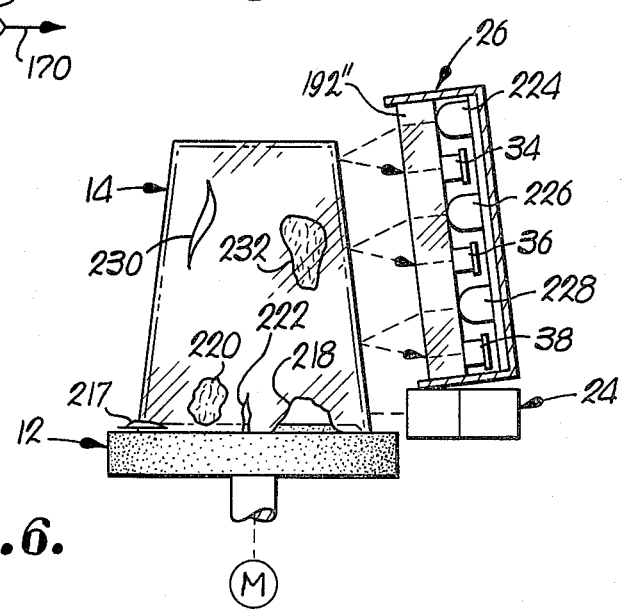
FIG. 6 is a largely schematic, side elevational depiction of another portion of the apparatus shown in FIG. 3, viewed as to the lower source and sensor assembly as from line 6—6 of FIG. 3, but with the upper source and sensor assembly being shown in vertical cross-section.

As will be better seen in FIGS. 4, 5 and 6, each rotatable turntable 12 has an associated shaft 172 operably coupled in suitable fashion indicated at 174 to an electric motor or the like 176 for rotating the same to turn an article 14 to be tested about its axis and relative to the associated light source 16 and/or sensor assemblies 18 et seq. The turntable 12 will preferably be provided with a raised central portion 178 for receiving and centering the article 14 in a predetermined position upon the turntable 12, so that the article 14 will be rotated substantially about its axis when the turntable 12 itself is rotated.

The light source 16 includes a frame 180 having base structure 182 for supporting a plurality of light emitting components such as incandescent lamps 184 that are electrically energized on a continuing basis in any suitable fashion during article testing operations. In the illustrated form of light source 16, three lamps 184 are shown, which is appropriate for articles 14 in the nature of plastic cups of a typical size, although it is to be understood that a greater or lesser number of lamps 184 may be provided to provide adequate illumination of the articles 14 to be tested, dependent upon the height of the latter. The light source 16 will also preferably include lens means as at 186 for directing the light from the lamps 184 toward the adjacent surface 188 of the article 14 to be tested. As illustrated, the lens means 186 may satisfactorily be formed from a single piece of approximately curved plastic material interposed between the lamps 184 and the surface 188, although separate lens for each lamp 184 could be employed, if desired.

The sensor assembly 18 may be constructed in generally similar and economical fashion, and includes a supporting frame 190 carrying lens means 192 behind which a plurality of light intensity sensing, photoelectric devices 34, 36 and 38 are mounted at appropriate heights, quite possibly upon the lens element 192 itself. Again, a greater or lesser number of the light intensity sensing devices 34 et seq. may be used, and separate lenses may be employed for the means 192 used to focus light transmitted through the article 14 and emanating from the surface 194 of the latter opposite from the light source 16 onto the photoelectric devices 34 et seq. that are provided. Electrical connections to the sensing devices 34 et seq. will be as shown in the electrical diagram of FIG. 1 and are not illustrated in the physical depiction of the sensor assembly 18 or the other sensor assemblies later described.

The article 14 shown in FIG. 4 is illustrated as having two types of faults including a tear in the body of the wall as at 196 and a "grease" spot of foreign material as at 198 adhering either to the inner or outer surface of the wall of the article 14. The sensor assembly 18 is adapted to most reliably sense faults in the article 14 in the nature of either such tears 196 or such grease spots 198. In either case, the sensor assembly 18 relies upon the interruption of light being transmitted from one or more of the lamps 184 of the light source 16 along paths as at 200, 202 and 204, which are directed through the article 14 and toward the corresponding fault sensing devices 34, 36 and 38. The interruption of any of such light paths 200 et seq. by either the light dispersing effect of a tear 196 or the light blocking effect of a grease spot 198 being rotated into an intersecting position therewith results in a sharp decrease in the intensity of light applied to the corresponding sensor(s) 34 et seq. and, in turn, in a decrease in the flow of source current to the node point 68 of the associated circuit 28 caused by the action of the corresponding sensor device(s) 34 et seq. in response to such decreased intensity of light reaching the same through the article 14.

The sensor assembly 20 is illustrated in FIG. 5 and may be in all respects constructed similarly to the sensor assembly 18, except that the frame 190' of the assembly 20 is preferably inclined slightly from vertical in the same general direction as the adjacent surface 194 of typical articles 14 to be tested. The sensor assembly 20, however, is primarily adapted for the detection of faults in the article 14 in the nature of grease spots as at 198' in a different way from the manner in which the sensor assembly 18 operates, which provides a further degree of reliability in the sensing of this difficult to detect type of fault in the article 14. Specifically, the sensing device(s) 34 et seq. of the sensor assembly 20 have only a relatively low level of ambient light applied thereto in the absence of a fault 198' in the article 14, by virtue of the inclination of the frame 190' and the focusing action of the lens means 192', which normally minimize the application of transmitted light along the paths 206 et seq. to the sensing devices 34 of the assembly 20. When the leading edge of a grease spot as at 198' moves into initial intersection with one of the paths of light 200 et seq. being transmitted through the article 14 from the light source 16, however, light will be diverted or reflected from such leading edge of the grease spot 198' in a manner typically resulting in a sharp increase in the intensity of light applied to the corresponding one of the sensing devices 34 et seq. Thus, the sensor assembly 20 is adapted to provide a second method of assuring the absence in articles 14 being inspected of faults in the nature of grease spots as at 198 or 198' in a manner entirely different both optically and electrically from the sensing for similar faults provided by the sensor assembly 18, since the latter senses a decrease in intensity of transmitted light from the source 16 due to interposition of the body of a grease spot while the assembly 20 senses an increase in intensity resulting from diversion or reflection of light from the source 16 off the leading edge of the grease spot. It should be noted that the sensor assembly 20 and the paths of diverted light 206, 208 and 210 detectable by the sensing devices 34 et seq. thereof are preferably disposed at an angle horizontally offset approximately 30° from the light paths 200, 202 and 204 along which light emanates from the lamps 184 of the light source 16, as best seen in FIG. 3.

The sensor assembly 22 may be constructed and supported in upright position in the same fashion previously described for the sensor assembly 18 illustrated in FIG. 4; however, as shown in FIG. 3, the sensor assembly 22 is located at an angle horizontally offset from the line of the light paths 200, 202 and 204 from the light source 16 of preferably about 80°, so that the sensor assembly 22 is oriented to receive light from the intersection of the paths 200 et seq. with the "back" side 194 of the article 14 at an angle more nearly perpendicular to the light paths at 200 et seq. than in alignment therewith. The operation of the sensor assembly 22 is also dependent upon light emanating from the light source 16 and transmitted through the "front" surface 188 of the article 14, but the sensor assembly 22 is primarily responsive to an increase in light intensity resulting from reflection off of an internal surface of a crack (as shown at 212 in FIG. 4) in the sidewall of the article 14, and it is for the reliable detection of this particular type of fault that the sensor assembly 22 is best adapted and may be provided. As those skilled in the art are aware, a crack as at 212 in the wall of an article 14 in the nature of a plastic cup or the like is typically more or less straight, may not involve the relative lateral offsetting of the adjacent portions of the wall of article 14, and is inherently relatively difficult to detect, either visually or by means of optical sensors. The sensor assembly 22, therefore, which relies upon a reflection from the crack of what is initially transmitted light, has been found to be a very worthwhile part of any quality control apparatus intended to detect this particular type of defect in articles 14.

It will be observed that the sensor assemblies 18, 20 and 22 all operate in response to changes in the intensity of light that initially emanates from the light source 16 and is then transmitted through at least a portion of the article 14 before being further transmitted or reflected by another portion of the article 14 to the particular one or more of the sensor assemblies 18, 20 and 22 that are adapted to respond to the particular type of fault involved. It necessarily follows that the sensor assemblies 18, 20 and 22 are inherently adapted for use only in testing articles 14 that are either transparent or highly translucent, since any transmittal of light from the source 16 would be blocked by the article 14, if the latter was fabricated from opaque material. For the purpose of testing opaque articles 14 for the existence of faults, therefore, it is necessary to utilize sensor assemblies such as at 24 and 26 that either include their own light source or are so juxtaposed with a light source and the opaque article 14 as to respond to the presence or absence of light reflected from such article 14. It has been found, however, that the use of reflected light for fault sensing purposes is optimum for the detecting of certain types of faults anyway, and ones that may not be as effectively sensed by the types of light intensity sensors relying upon transmitted light, so that the inclusion in the involved type of testing apparatus of sensors that are responsive to reflected light has been found desirable even for the testing of transparent articles 14, as well as for the purpose of rendering the apparatus capable of testing either transparent or opaque type articles 14.

With reference to both FIGS. 3 and 6, the sensor assembly 24 may preferably include only a single incandescent lamp source 214 and a single photoelectric sensing device 216, which are both disposed at a level and oriented to focus upon a zone of the wall of the article 14 that is adjacent the normally open mouth end of the latter supported on the turntable 12. Certain types of faults that are relatively common in the production of the involved class of articles 14 occur most frequently along the lip or open mouth end of the article 14; these include so-called "flashes" as at 217 involving extra material left protruding from the lip during the molding process and so-called "short shots" or voids as at 218 in the nature of typically irregular notches in the lip of the article 14 at the open mouth end of the latter. Grease spots as at 220 and tears as at 222 are also among the types of faults that may occur along or adjacent the open extremity of the article 14. The response of the sensor assembly 24 and particularly the photoelectric sensing device 216 employed thereby is quite different depending upon the nature of the fault encountered. For a short shot type fault as at 218, the void in the material of the article 14 gives rise to a discontinuity in the reflection of light from the source 214 to the sensing device 216, thereby sharply decreasing the intensity of light applied to the latter and resulting in a decreased flow of current through the sensing device 216 (which corresponds electrically to the sensing device 34 shown and described in connection with FIG. 1 and the detection circuitry 28). On the other hand, flashes of extra material as at 217 typically result in increased reflection by the article 14 of light from the source 214 to the sensing device 216, a sharp increase in the intensity of light applied to the latter and an increase in current flow through the latter. With the reflection sensing technique utilized by the sensor assembly 24, the grease spots that are most reliably detectable are those occurring on the outer surface of the article 14. Such an outside grease spot may, however, produce either a sharp increase or a sharp decrease in the intensity of light applied to the sensing device 216, depending upon the nature of the foreign material presenting the grease spot. Accordingly, the sensor assembly 24 may react to an outside grease spot either in terms of a sharp increase in current flow through the sensing device 216 or a sharp decrease in such current flow, which further illustrates and emphasizes the importance of the detection circuitry 28 being adapted to respond equally well and in similar fashion to either of such fault indicating conditions. Tears as at 222 along the lip of the article 14 similarly may react upon the sensing device 216 either in terms of an increase in the intensity of the reflected light or a decrease in such intensity or even an increase followed by a decrease or vice versa depending upon the nature of the tear. Again, however, the adaptability of the detection circuitry 28 for responding to changes in either directions of the intensity of light being applied to a sensing device such as at 216 from the intensity to which such device is normally subjected during quiescent or no-fault conditions renders the improved reliability provided by the testing apparatus of the invention feasible.

The sensor assembly 26 shown in FIG. 6 is similar in general construction to the previously described sensor assembly 20 illustrated in FIG. 5, except that, in addition to the sensing devices 34, 36 and 38, the assembly 26 includes an incandescent light source as at 224, 226 and 228 for each of such sensing devices respectively, it being understood that suitable lens means 192" are also included for appropriately directing the path of light from each of the sources 224 et seq. toward the article 14 and for reflection back from the latter to the corresponding sensing device 34 et seq. As shown in FIG. 6, the sensor assembly 26 may conveniently be disposed directly above the sensor assembly 24, although it will be perceived that this is not necessary and that the assembly 26, being self-contained with its own light sources, could be elsewhere located in proximity to the article 14. The sensor assembly 26, which is adapted for use in testing either transparent or opaque articles 14, is very reliable and primarily adapted for the detection of tears as at 230 or outside grease spots as at 232. A tear is sensed by the assembly 26 in terms of a sharp decrease in the intensity of the light being reflected to the involved one or more of the sensing devices 224 et seq. The detection of an outside grease spot by the assembly 26, however, is dependent upon the foreign material presenting the grease spot, which may result in either a significant increase of a significant decrease in the intensity of light being reflected to the involved sensing device(s) 224 et seq. Again, the significance of the ability of the detection circuitry 28 to cope with faults producing either increases or decreases of light intensity and to do so in a manner providing a consistent fault indicating output in either case will be appreciated.

In an optimized version of the apparatus contemplated by the invention, which is to be adapted to inspect either transparent or opaque articles 14 for the detection of faults therein, all of the sensor assemblies 18, 20, 22, 24 and 26 may be provided, and, even though certain of such assemblies 18 et seq. may be adapted for sensing the existence of overlapping categories of faults, the differing fashions in which the various sensor assemblies 18 et seq. respond to particular types of faults tends to increase reliability with a minimum of what might otherwise be considered to constitute redundancy. In any event, the relative simplicity of the sensor assemblies 18 et seq. and the economy with which each of the same may be fabricated and installed as a part of the overall fault detecting apparatus will normally make it desirable to include all or as many of same in the apparatus as might be applicable for the testing of the particular types of articles 14 to be inspected. It is recognized of course, however, that particular applications, such as where only opaque type articles 14 are to be inspected, might dictate the employment of some appropriate subgroup of the sensor assemblies 18 et seq. Even in such instances, it should be clear that the combination whichever of the sensor assemblies 18 et seq. that are utilized with the detection circuitry 28 that is adapted to reliably and consistently respond to either increases or decreases in the intensity of either transmitted or reflected light will provide a greatly improved form of apparatus for testing the involved type of articles, as compared with anything that has heretofore been available for such purposes.

Those skilled in the art will readily recognize that various minor modifications could be made to the currently preferred form of the apparatus contemplated by the invention, as hereinabove disclosed for illustrative purposes, without departing from the essence of the invention and while still enjoying the improved results made possible thereby. Accordingly, it is to be understood that the invention should be deemed limited only by the fair scope of the claims which follow when construed to include mechanical equivalents thereof.

I claim:

1. In apparatus for detecting fault conditions in plastic articles such as molded containers or the like:
   means for supporting an article to be checked and for rotating the same about an axis of symmetry thereof;
   means for directing light radiations toward said article;
   means for receiving light radiations after the latter have encountered said article and for varying the magnitude of an electrically significant parameter from a predetermined normal level thereof in correlated relationship with changes in the intensity of said received light radiations; and
   means electrically coupled with said receiving means and responsive to changes in the magnitude of said parameter for producing an output signal indicative of detection of a fault condition in said article, said signal being in the nature of an electrical pulse of predetermined polarity whenever the magnitude of said parameter is varied by said receiving means by at least a predetermined amount from said normal level in either the direction of exceeding said normal level or the direction of being exceeded by said normal level,
   said receiving means comprising at least one photosensitive device, the internal electrical impedance through which varies in correlated relationship with the intensity of light applied to said device and in response thereto, said signal producing means including
- a direct current energized electrical circuit couplding said device in series with a resistance and presenting a node point therebetween, the electrical potential at said node point being affected by the amount of electrical current flowing thereto through said device, said current normally being at an intermedite, quiescent level in the absence of faults in said article,
- electrical current sink means coupled with said node point for carrying electrical current away from the latter when said sink means is activated and having a control terminal for electrically activating the same,
- first voltage comparator means having an input terminal electrically coupled with said node point, a reference terminal electrically coupled with a source of reference potential substantially equivalent to said quiescent level, and an output terminal,
- electrical feedback path circuit means for coupling said output terminal of said first comparator means with said control terminal of said sink means, and
- second voltage comparator means having an input terminal electrically coupled with said node point, a reference terminal electrically coupled with a source of reference potential less than said quiescent level, and an output terminal,
- said first and second comparator means being operated relative to their respective differential voltage transfer characteristics for supplying a feedback signal from said output terminal of said first comparator means to said control terminal of said sink means for activating the latter whenever the electrical potential at said node point rises above the reference potential applied to said reference terminal of said first comparator means and for presenting a fault indicating signal at said output terminal of said second comparator means whenever the electrical current input to said node point varies either substantially above or substantially below said quiescent level.

2. Apparatus as set forth in claim 1, wherein:
said fault indicating signal presented at said output terminal of said second comparator means is of like polarity and similar pulse-like waveform both for faults causing an increase in the intensity of light applied to said device and for faults causing a decrease in the intensity of light applied to said device.

3. Apparatus as set forth in claim 1, wherein:
there are provided means for selectively adjusting the level of said potential applied to said reference terminal of said first comparator means.

* * * * *